US012318202B2

(12) United States Patent
Mena Benito et al.

(10) Patent No.: US 12,318,202 B2
(45) Date of Patent: Jun. 3, 2025

(54) SYSTEM AND METHOD FOR MONITORING A STATE OF WELL-BEING

(71) Applicant: KONINKLIJKE PHILIPS N.V., Eindhoven (NL)

(72) Inventors: Maria Estrella Mena Benito, Eindhoven (NL); Ihor Olehovych Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 720 days.

(21) Appl. No.: 16/490,727

(22) PCT Filed: Feb. 27, 2018

(86) PCT No.: PCT/EP2018/054757
§ 371 (c)(1),
(2) Date: Sep. 3, 2019

(87) PCT Pub. No.: WO2018/162279
PCT Pub. Date: Sep. 13, 2018

(65) Prior Publication Data
US 2020/0015728 A1  Jan. 16, 2020

(30) Foreign Application Priority Data
Mar. 8, 2017  (EP) .................................... 17159771

(51) Int. Cl.
*G16H 40/67* (2018.01)
*A61B 5/00* (2006.01)
(Continued)

(52) U.S. Cl.
CPC ............ *A61B 5/165* (2013.01); *A61B 5/0077* (2013.01); *A61B 5/0205* (2013.01); *G16H 40/67* (2018.01);
(Continued)

(58) Field of Classification Search
CPC ..... A61B 5/165; A61B 5/0077; A61B 5/0205; A61B 5/02125; A61B 5/02427;
(Continued)

(56) References Cited

U.S. PATENT DOCUMENTS 7,547,279 B2  6/2009 Kim
9,757,065 B1*  9/2017 Suri ....................... A61B 1/247
(Continued)

FOREIGN PATENT DOCUMENTS

CN  104257434  1/2015
CN  204650264  9/2015
(Continued)

OTHER PUBLICATIONS

"Liu, et al., A Review of Non-Contact, Low-Cost Physiological Information Measurement based on Photoplethysmographic Imaging, Sep. 1, 2012, IEEE, 34th Annual International Conference of the IEEE EMBS, pp. 2088-2091" (Year: 2012).*
(Continued)

*Primary Examiner* — Jennifer Pitrak McDonald
*Assistant Examiner* — Michael T. Holtzclaw

(57) ABSTRACT

The present disclosure relates to a system for monitoring a state of well-being of an individual. The system includes a remotely operating camera-based sensing unit including at least one image sensor arranged to remotely monitor a skin portion of a user and a close-up sensing unit provided at a hand-held personal care appliance. The close-up sensing unit is arranged to monitor a physiological signal of the user. The monitoring of the physiological signal is temporally aligned with the remote monitoring of the skin portion of the user. The system also includes a control unit arranged to process first sensor data provided by the remotely operating camera-based sensing unit and second sensor data provided by the close-up sensing unit.

20 Claims, 6 Drawing Sheets

(51) Int. Cl.
  *A61B 5/0205* (2006.01)
  *A61B 5/021* (2006.01)
  *A61B 5/024* (2006.01)
  *A61B 5/08* (2006.01)
  *A61B 5/16* (2006.01)

(52) U.S. Cl.
  CPC ....... *A61B 5/02125* (2013.01); *A61B 5/02427* (2013.01); *A61B 5/0816* (2013.01)

(58) Field of Classification Search
  CPC ....... A61B 5/0816; A61B 5/01; A61B 5/0533; A61B 5/6898; A61B 5/4884; A61B 5/14551; G16H 40/67; G16H 40/63; G16H 10/60; G16H 50/30; A61C 17/16; A61C 17/221
  See application file for complete search history.

(56) References Cited

U.S. PATENT DOCUMENTS

| | | | |
|---|---|---|---|
| 2007/0027386 A1* | 2/2007 | Such | A61B 5/0006 600/509 |
| 2013/0091642 A1 | 4/2013 | Dykes | |
| 2014/0121540 A1* | 5/2014 | Raskin | A61B 5/0205 600/479 |
| 2015/0112452 A1* | 4/2015 | He | A61B 5/7282 700/11 |
| 2015/0265212 A1* | 9/2015 | Bruekers | A61B 5/02416 600/301 |
| 2016/0188831 A1 | 6/2016 | Kurtz | |
| 2016/0278644 A1* | 9/2016 | He | A61B 5/02125 |
| 2016/0302679 A1 | 10/2016 | De Haan | |
| 2017/0055853 A1 | 3/2017 | Kirenko | |
| 2017/0055907 A1* | 3/2017 | Altebaeumer | A61B 5/02416 |
| 2017/0188885 A1* | 7/2017 | Banet | A61B 5/0537 |
| 2019/0090816 A1* | 3/2019 | Horseman | G16H 50/30 |
| 2020/0085312 A1* | 3/2020 | Tzvieli | A61B 5/7282 |

FOREIGN PATENT DOCUMENTS

| | | |
|---|---|---|
| JP | 2009153609 A | 7/2009 |
| JP | 2014000105 A | 1/2014 |
| WO | 2005/006968 | 1/2005 |
| WO | 2014002418 A1 | 1/2014 |

OTHER PUBLICATIONS

"Sun, et al., Photoplethysmography Revisited: From Contact to Noncontact, From Point to Imaging, Mar. 2016, IEEE Transactions on Biomedical Engineering, vol. 63, No. 3, pp. 463-477" (Year: 2016).*

"Bousefsaf, et al., Remote assessment of physiological parameters by non-contact technologies to quantify and detect mental stress states, 2014, 2014 International Conference on Control, Decision and Information Technologies (CoDIT), pp. 719-723" (Year: 2014).*

International Search Report and Written Opinion Dated Apr. 25, 2018 for International Application No. PCT/EP2018/054757 Filed Feb. 27, 2018.

Maurizio Pesce: "Oral-B's App-Enabled Toothbrush Exposes Your Poor Hygiene l Wired", Feb. 21, 2016 (Feb. 21, 2016), XPO55370349, Retrieved from the Internet: URL:https://web-beta.archive.org/web/20160221224305i d_/https://www.wi red.com/2016/02/oral-b-genius-toothbrush/.

Verkruysse et al: "Remote plethysmographic imaging using ambient light", Optics Express, 16 (26), Dec. 22, 2008, pp. 21434-21445.

Wieringa, et al: "Contactless Multiple Wavelength Photoplethysmographic Imaging: A First Step Toward "SpO2 Camera" Technology," Ann. Biomed. Eng. 33, 1034-1041 (2005).

Vinkers, et al: "The effect of stress on core and peripheral body temperature in humans", Stress. Sep. 2013; 16(5):520-30.

Herborn, et al: "Skin temperature reveals the intensity of acute stress", Physiology & Behavior, vol. 152, Part A, Dec. 1, 2015, pp. 225-230.

Mcduff, et al: "Remote Measurement of Cognitive Stress via Heart Rate Variability".

Sun, etl al: "Activity-aware mental stress detection using physiological sensors." Mobile computing, applications, and services. Springer Berlin Heidelberg, 2010. 211-230.

Silbert, "Mit Media Lab's Medical Mirror Can Read Your Pulse" Jan. 16, 2011 http://www.laptopmag.com/articles/mit-media-labs-medical-mirror-can-read-your-pulse.

Poh, et al: "A medical mirror for non-contact health monitoring." ACM SIGGRAPH 2011 Emerging Technologies. ACM, 2011.

Jovin, "Seizure and stress detecting Embrace wearable starts shipping" Mar. 10, 2016 http://gadgetsandwearables.com/2016/03/10/empatica-embrace/.

Hodson, "Smart mirror monitors your face for telltale signs of disease", Jul. 2015.

* cited by examiner

SYSTEM AND METHOD FOR MONITORING A STATE OF WELL-BEING

CROSS REFERENCE TO RELATED APPLICATIONS

This application is the U.S. National Phase application under 35 U.S.C. § 371 of International Application No. PCT/EP2018/054757 filed Feb. 27, 2018, published as WO 2018/162279 on Sep. 13, 2018, which claims the benefit of European Patent Application Number 17159771.9 filed Mar. 8, 2017. These applications are hereby incorporated by reference herein.

FIELD OF THE INVENTION

The present disclosure relates to a system for monitoring a state of well-being of an individual that implements a remotely operating sensing unit and a close-up sensing unit. More particularly, but not to be understood in a limiting sense, the present disclosure relates to systems for stress monitoring or stress detection that utilize unobtrusively obtained information to assess the state of well-being of the observed object.

More particularly, the present disclosure relates to a system of monitoring a state of well-being that is operable in a home-user environment and that is particularly easy to use, preferably on a day by basis.

The present disclosure further relates to a corresponding method of monitoring a state of well-being of an individual, and to a related computer program.

BACKGROUND OF THE INVENTION

US 2017/0055853 A1 discloses a wearable device for obtaining signals from a subject incorporating a first, contact PPG sensing unit and a second, remote PPG sensing unit, wherein the first and the second PPG sensing unit are both integrated in the wearable device and acquire PPG signals from different locations of a user's body.

The internet article "Oral-B's App-Enabled Toothbrush Exposes Your Poor Hygiene" by Maurizio Pesce (XP055370349, https://web-beta.archive.org/web/20160221224305id_/https://www.wired.com/2016/02/oral-b-genius-toothbrush/) relates to a toothbrush that can be combined with a smartphone to identify a user and to guide the user through the teeth brushing procedure.

US 2013/0091642 A1 discloses an oral health care implement, comprising a handle having a distal end, a middle portion, and a proximal end; an oximetry sensor having at least one light emitter and at least one photo detector and is configured to determine a condition of the user chosen from the group blood oxygen saturation, heart rate, and any combination thereof; a data processing unit having a collector, a storage medium, and a processor; and a power source, wherein the oximetry sensor is configured to transmit at least one signal indicative of oximetry to the data processing unit.

WO 2005/006968 A1 discloses a portable electronic device arranged to be brought into a contact with an individual's skin when being used by said individual, said device comprising a first contact surface and a second contact surface, wherein the first contact surface comprises a first electrode and the second contact surface comprises a second electrode, said first electrode being electrically isolated from said second electrode; the device further comprising means for measuring an electrical signal from said first electrode and said second electrode during the usage of said device, said electrical signal being representative of a physiological condition of said individual.

Stress may generally be referred to as an individual's response to stressing events. In other words, stress is a human being's method of reacting to and coping with challenges. As used herein, stress shall be regarded as an exemplary representative of a variety of states of well-being of an individual. Therefore, the fact that often reference is made to stress or stressing events herein shall not be interpreted in a limiting sense.

In nowadays life, chronic stress has become a serious problem for many people. Nowadays, people are subjected to numerous stressors that are present in their daily life. Hence, many individuals are in a more or less permanent state of stress. Chronic stress, however, is problematic as human beings (as well as animals) are basically not prepared to suffer long-lasting periods of stress. An increased stress level may give rise to a wide range of health-related diseases, such as cardiovascular diseases, cerebrovascular diseases, diabetes, and immune-deficiencies, for instance.

In addition to physiological diseases, stress may also give rise to mental diseases. In a worst case scenario, chronic stress may cause or amplify serious mental illnesses, such as anxiety disorders, depressions, and such like.

It is therefore generally desirable to monitor and assess an individual's current stress level, and to track and plot the stress level over time. In this way, periods of increased stress may be detected and, preferably, predicted before the actual stress level becomes too high. Hence, if an individual is aware of an increasing or already increased stress level, appropriate counter measures may be taken, including some relaxing, having a sleep, getting some positive distraction, getting some exercises or other leisure activities, and such like.

Further, as more and more people are permanently suffering from an increased stress level, being aware of one's current stress level becomes more and more important. Measuring chronic stress is rather difficult as individuals differently respond to stressors. Further, there is a certain grey area or transition zone between a relaxed state and a seriously stressed state.

There exist several approaches to stress measurement. By way of example, stress detection can be conducted based on an interview with a physician or a psychologist. Generally, mental and physiological symptoms of a chronic stress state may be assessed using a questionnaire and/or interrogation techniques. However, this approach is insofar limited as only an actual state provides the basis for the analysis. Hence, even if one may ask the individual about a trend or course of the stress level over a certain past period, any answer is somewhat biased and distorted.

It is therefore desirable to present approaches to continuous monitoring of individuals' stress symptoms which may involve spot measurements on a daily or weekly basis, for instance.

A number of physiological markers (signals) have been identified as potential indicators for the stress level of an individual. These markers include, but are not limited to, galvanic skin response, blood pressure, respiration activity, heartbeat, including the detection of characteristic features in the heartbeat curve, etc.

In this context, monitoring devices have been proposed that are arranged to detect one or more of these physiological markers. Hence, it is basically possible to detect and track changes in the involved vital signs to detect potentially problematic values and patterns. However, measuring and monitoring a stress level in this way involves some discrete and time-consuming measurements, using complex stand-alone devices.

Hence, even though the above-mentioned approach is reasonable and useful to detect problematic states of well-being of individuals, the application of these techniques is still somewhat limited.

Further, when an individual already experienced an increased stress level, even the generally advisable distinct stress level monitoring may be experienced as even further stressing, since it generally takes some time and concentration to perform the measurements.

Hence, there is still room for improvement in stress monitoring and stress detection, particularly in home-user environments.

SUMMARY OF THE INVENTION

It is an object of the present disclosure to provide alternative and improved approaches to stress monitoring and stress measurements. Preferably, the stress level and changes of the stress level of an individual can be monitored on a regular basis in a home user environment. Preferably, stress monitoring may be performed in a basically comfortable and non-obtrusive fashion. Further, it is desirable to present an approach to stress monitoring that is not time-consuming and that may be applied as a part of the daily routine of an individual. Preferably, the stress level monitoring procedures may form part of the daily personal care routine.

Further, it is desirable to present approaches to stress monitoring that are robust and less susceptible to distortions. Further, it is desirable to present a respective system that is operable with a considerable level of accuracy even with unexperienced users.

It would be further beneficial to present a corresponding method of monitoring a state of well-being of an individual, and a corresponding computer program.

In a first aspect of the present disclosure there is presented a system for monitoring a state of well-being of an individual, the system comprising:

two distinct sensing units comprising
a remotely operating sensing unit comprising at least one image sensor arranged to remotely monitor a skin portion of a head region of a user, and
a close-up sensing unit provided at a hand-held personal care appliance, the close-up sensing unit being arranged to monitor a physiological signal of the user through a contact with the hand of the user,
wherein the monitoring of the physiological signal is temporally aligned with the remote monitoring of the skin portion of the user, and
a control unit arranged to process first sensor data provided by the remotely operating sensing unit and second sensor data provided by the close-up sensing unit,
wherein the control unit is arranged to process, based on the processed first sensor data and second sensor data, at least one well-being parameter,
wherein the control unit is arranged to provide, based on the at least one processed parameter, well-being information that is indicative of a current stress level of the user, and
wherein the system is operable while performing a personal care procedure with the personal care appliance.

This aspect is based on the insight that a rather accurate and robust measurement environment may be provided when, on the one hand, a device is used that is anyway grabbed and held by the individual. Further, to augment the measurement and to provide a broader signal basis, it is proposed to use a further, remotely operating sensor unit. Hence, the required level of user interaction is greatly reduced. Rather, due to the first sensor unit and the second sensor unit, considerably precise and accurate measurements are possible.

Each of the sensing units may incorporate one or more sensors. Generally, the one or more sensors may be arranged in accordance with existing principles for sensors that are applicable in the context of stress measurement and stress management. As indicated above, there exist several symptoms that are basically indicative of the stress level. For instance, signals such as blood pressure, blood volume pulse, galvanic skin response, and such like may be used for obtaining the at least one parameter that is indicative of the stress level.

In some embodiments, the control unit is arranged to process at least two well-being parameters. At least one of the parameters is primarily based on information provided by the remotely operating sensing unit. At least one of the parameters is primarily based on information provided by the close-up sensing unit.

It has been further observed, that also PPG (photoplethysmography) measurements allow the derivation and calculation of potentially stress level indicative signals. Further, remote photoplethysmography monitoring techniques have been proposed. Devices that are used to this end are generally camera based, i.e. utilize a plurality of sensing elements, such as CCD-elements, CMOS-elements, and such like. In contrast to contact photoplethysmography measurements which typically focus on a restricted local area, remote photoplethysmographic monitoring allows to monitor a rather large region of an observed individual. As a side effect, this allows for the detection of local discrepancies and characteristics. For instance, a spatial distribution of amplitudes and phase differences of the detected signals may contain valuable information about micro-perfusion or micro-circulation.

Generally, using two rather distinct sensor units one of which is a remotely operating sensing unit, while the other one is a close-up sensing unit enables to obtain a set of signals that represent a plurality of mental/physiological health parameters.

When camera-based PPG techniques are applied, visual information about the pulse transit time over a certain body region may be detected. Further, when two sensor units are used one of which is, for instance, hand-held while the other one is, for instance, observing the face of the user, information from two rather remote and distinct body regions may be obtained.

A further advantage of the above arrangement is that a set of sensors may be used without further obtruding or disturbing the user.

Assuming that the measurement and detection of the stress level of the user may be repeated on a daily basis, for instance as a part of the daily personal care routine, a mid-term or long-term stress level record may be obtained.

As used herein, the term temporally aligned includes, but is not limited to, a synchronized and/or simultaneous detection of signals. Preferably, the temporally aligned signals are sufficiently accurate to enable enhanced phase shift processing and similar signal processing measures. In this way, a potential phase shift between the involved signals, that are accurately aligned, may be processed to detect at least one of PTT (Pulse transit time) signals, PAT (Pulse arrival time) signals, and further cardiovascular information/signals that are indicative of the state of well-being of the user, for instance. In some embodiments, the first sensor data, which is provided by the remotely operating sensing unit, may be image data. Generally, a camera-like sensor unit may be used for image capturing. Image data may be obtained in the visible range and/or the invisible range of electromagnetic radiation.

In some embodiments, the second sensor data that is provided by the close-up sensing unit may be referred to as supplemental sensor data. In some embodiments, the well-being parameter is computed based on both image data and supplemental sensor data. Supplemental sensor data may include data acquired through spot measurements that do not involve image detection.

In some embodiments, the remotely operating sensing unit and the close-up sensing unit are arranged to monitor, respectively, first and second skin portions of a user, the skin portions being different. By way of example, this is beneficial in the context of phase shift processing, as a phase shift in cardiovascular signals obtained from different body portions may be detected.

The system is operable while performing a personal care procedure with the personal care appliance. Hence, stress level detection or, more generally, detection of a state of well-being may be performed without or with only little additional effort on the part of the user. In particular, the period that is anyway necessary for the personal care procedure may be used to detect the state of well-being.

In an exemplary embodiment, the remotely operating sensing unit is a camera based remote PPG sensing unit that is arranged to obtain signals based on which the user's pulse rate and respiration rate is detected, wherein the close-up sensing unit is a contact PPG sensing unit, wherein the remotely operating sensing unit and the close-up sensing unit are arranged to monitor two distinct and remote body regions of the user, wherein the control unit is arranged to calculate the pulse transit time based on PPG information obtained from the two body regions, and to calculate the blood pressure based on the pulse transit time. In this context, reference is made to US 2017/0055853 A1, describing general approaches to the calculation of blood pressure information based on pulse transit time information.

In a further exemplary embodiment, the remotely operating sensing unit is arranged to detect and the control unit is arranged to process image data in the visible range and in the non-visible range. As used herein, the visible range covers a portion of the electromagnetic spectrum that is typically visible to the human eye.

Hence, the visible range may for instance involve a range from about 390 nm (nanometers) to about 700 nm. Adjacent to the visible range, the infrared range and the ultraviolet range is provided. Infrared radiation covers radiation having longer wavelengths than those of the visible light. Depending on the respective definition, infrared light may cover the range between about 700 nm and about 1,000 μm (micrometer). In practice, primarily a so-called near-infrared radiation is used which may cover, depending on the definition, a range between about 700 nm and 1,400 nm.

Ultraviolet radiation is electromagnetic radiation having shorter wavelengths than those of visible light and may cover a range of about 10 nm to about 390 nm. Needless to say, there is no sharp border between the respective regions of the electromagnetic radiation.

Providing the sensing unit and the control unit with the capability of processing non-visible radiation has the advantage that stress level indicative information may be detected that is not clearly visible to the human eye. Hence, emerging stress indicators may already be detected in a state where they are not visible to the human eye. It may be therefore beneficial to utilize not only a visible radiation portion but also invisible radiation portions as in this way a greater penetration depth (in the skin) may be achieved.

In a further exemplary embodiment, the remotely operating sensing unit is arranged to monitor a head portion of the user, particularly a face poriton. Attaching obtrusively operating sensors to the head is often experienced as being unpleasant. Therefore, an unobtrusive, contactless measurement is appreciated for the head portion. Further, as the remotely operating sensing unit preferably incorporates at least one camera based sensor, it is not necessary to remain in a steady position in front of the remotely operating sensor unit which, again, is often experienced as being unpleasant.

In a further exemplary embodiment, the at least one image sensor of the remotely operating sensing unit is arranged at or in the vicinity of a mirror. For instance, the remotely operating sensing unit may be integrated in a bathroom mirror or at least arranged in the vicinity thereof. In some embodiments, the remotely operating sensing unit may be integrated in a mirror. This has the advantage that the remotely operating sensing unit is not visible or only barely visible from the front of the mirror.

In a further exemplary embodiment, the remotely operating sensing unit is arranged as a remote photoplethysmography sensing unit, and wherein the close-up sensing unit is arranged as a contact photoplethysmography (PPG) sensing unit. Hence, perfusion-related or, more generally, information about the circulatory system of the user, may be obtained from two rather distinct body regions. Based on this, spatial discrepancies may be detected.

In one exemplary setup, the remotely operating sensing unit comprises at least one remote photoplethysmography sensor. Further, the close-up sensing unit comprises at least one contact photoplethysmography sensor. In addition, the close-up sensing unit may comprise a galvanic skin response sensor, and a temperature sensor. Further types of supplemental sensors are conceivable.

Needless to say, the remotely operating sensing unit may be capable of thermal imaging. In this way, also the remotely operating sensing unit may be capable of temperature sensing.

Based on the contact PPG sensor, pulse information may be obtained. This may be referred to as baseline pulse signal. Based on the galvanic skin response sensor, a current sweat level at the skin of the user's hand may be detected. Based on the temperature sensor, a current temperature of the user's hand may be detected. The afore-mentioned sensors of the close-up sensing unit may be operated without further disturbing the user.

In addition, also the remotely operating sensing unit may be operated without requesting the user to attach sensor equipment, to remain in a steady state, etc.

In a further exemplary embodiment, the control unit is arranged to process photoplethysmography information obtained from different body regions of the user.

In a further exemplary embodiment, the remotely operating sensing unit is arranged to detect a first PPG signal based on which a pulse rate and a respiration rate is obtained, wherein the close-up sensing unit is arranged to detect a second PPG signal based on which a blood pressure parameter is obtained.

In a further exemplary embodiment, the control unit is arranged to detect and analyze differences between characteristics of the first PPG signal and the second PPG signal.

In a further exemplary embodiment, the first PPG signal involves a 2D PPG distribution, and wherein the control unit is arranged to detect spatial discrepancies in the first PPG signal.

In a further exemplary embodiment, the control unit is arranged to process a set of stress level indicative parameters, to perform a threshold analysis for the set of parameters, and to determine, based thereon, a current stress level of the user.

In a further exemplary embodiment, at least one of the remotely operating sensing unit and the close-up sensing unit is arranged to detect body temperature indicative information. Further, temperature differences between different measurement sites may be detected.

In a further exemplary embodiment, the remotely operating sensing unit is provided with or operatively coupled to at least one illumination source that is operable to illuminate the monitored head portion of the user.

As with the remotely operating sensing unit, also the at least one illumination source may be integrated in or arranged adjacent to the mirror. In some embodiments, an environmental illumination is used. However, in some alternative embodiments, specific illumination sources are used that are adapted to the spectral responsivity of the at least one sensor of the remotely operating sensor unit.

Further, as with the remotely operating sensing unit, in some embodiments, at least one illumination source is embedded or integrated in a mirror. Hence, in a power off state, the illumination source is not necessarily visible from the front of the mirror.

In a further exemplary embodiment, the hand-held personal care appliance is one of a grooming appliance, a dental care appliance, a massage appliance, and a skin care appliance.

By way of example, the personal care appliance that incorporates the close-up sensing unit may be arranged as a mouth care appliance, a toothbrush appliance, a grooming appliance, a shaving appliance, a trimming appliance, a vibrating appliance, a massage appliance, and such like. Further, it is conceivable that the personal care appliance is arranged as an epilator.

By way of example, using a motor powered toothbrush form part of the daily routine and is typically used twice in a day, in the morning and in the evening. Therefore, it is beneficial to incorporate the close-up sensing unit in a toothbrush or a similar personal care appliance. In this way, as the user brushes his/her teeth, as a beneficial side effect, a set of potentially indicative signals is detected. This may involve pulse related information, skin temperature, a sweat level, etc.

In addition, as tooth brushing is typically performed in front of a mirror, the remotely operating sensing unit may obtain further information, particularly photoplethysmography information, when observing a head portion of the user.

The control unit may be operatively coupled with both the remotely operating sensor unit and the close-up sensor unit. By way of example, a control unit may be provided that is integrated in or attached to the mirror and therefore hardwired to the remotely operating sensing unit and, if any, the illumination unit. However, this shall not be interpreted in a limiting sense.

Therefore, alternative embodiments may be envisaged, wherein the control unit is arranged as a distributed control unit having several sub-entities that are arranged at or coupled to the remotely operating sensing unit and the close-up sensing unit.

Further, in at least some embodiments, it is conceivable to use a separate computing device that incorporates the control unit. To this end, a mobile computing device such as a mobile phone, a mobile computer, a tablet computer, and such like, may be used. In either case, the control unit is operatively coupled to the remotely operating sensing unit and the close-up sensing unit, for instance via wireless communications.

In some embodiments, the control unit is arranged to detect and calculate blood pressure values and related signals. Further, a so-called pulse transit time (PTT) between photoplethysmography (PPG) values of the region that is observed by the remotely operating sensing unit and the region that is observed by the close-up sensing unit may be calculated.

Further, the control unit may be arranged to detect differences and changes in skin temperature, again observing two separate regions, for instance the face and the hand/palm of the user.

In some embodiments, the control unit is further arranged to detect characteristic changes in the perfusion (hemodynamics) in or beneath the skin tissue. Again, characteristic differences between the observed regions may be detected. Further, to accomplish an exemplary set of parameters, the heart rate and the respiration rate may be detected.

The set of values and information obtained in this way may be compared with earlier measurements.

In a further aspect of the present disclosure there is presented a method of monitoring a state of well-being of an individual, the method comprising:
provides two distinct sensing units (30, 56) comprising:
    providing a remotely operating sensing unit that comprises at least one image sensor arranged to remotely monitor a skin portion of a head region of a user,
    providing a hand-held personal care appliance that is equipped with a close-up sensing unit that is arranged to monitor a physiological signal of the user,
wherein the monitoring of the physiological signal is temporally aligned with the remote monitoring of the skin portion of the user through a contact with the hand of the user,
providing a control unit that arranged to process first sensor data provided by the remotely operating sensing unit and second sensor data provided by the close-up sensing unit,
performing a personal care operation with the personal care appliance,
processing, based on the processed first sensor data and second sensor data, at least one well-being parameter while performing a personal care procedure with the personal care appliance, and
calculating, based on the at least one processed parameter, well-being information that is indicative of a current stress level of the user.

In still another aspect of the present disclosure, there is presented a computer program comprising program code means for causing a system in accordance with the present disclosure to carry out the steps of the operating method as described herein when said computer program is carried out on a computing device that is operatively coupled with or forms part of the monitoring system.

Preferred embodiments of the disclosure are defined in the dependent claims. It shall be understood that the claimed method has similar and/or identical preferred embodiments as the claimed system and as defined in the dependent claims

BRIEF DESCRIPTION OF THE DRAWINGS

These and other aspects of the disclosure will be apparent from and elucidated with reference to the embodiments described hereinafter. In the following drawings

DETAILED DESCRIPTION OF THE INVENTION

Figure 1:
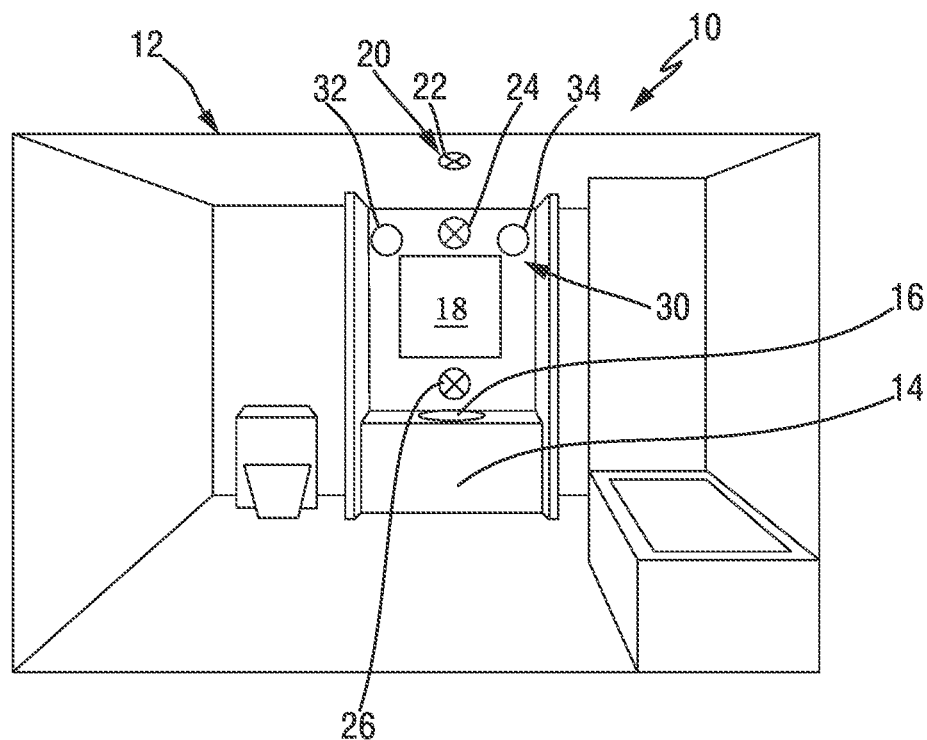
FIG. 1 shows a simplified schematic perspective view of an exemplary setting of a personal care system implemented in a bathroom.

FIG. 1 is a schematic perspective view of an exemplary personal care setting 10 which is provided in a bathroom 12. In the bathroom 12, a washbasin 14 is present that includes a sink 16. Above the sink, a mirror 18 is present which may also be referred to as bathroom mirror. A user may assume a position in front of the mirror 18 and then perform a personal care treatment, for instance a shaving operation.

A personal care procedure typically involves handling a movable hand-guided appliance. This may involve approaching and contacting processing zones at the user, involving the mouth portion, the facial region, the neck region, the chin region, the hair region/scalp region, further body parts, etc. Hence, an adequate illumination of the processing zone is appreciated to facilitate handling the appliance.

An illumination unit is indicated in FIG. 1 by 20. The illumination unit 20 involves a top or ceiling light source 22 that is arranged at a ceiling in front of the mirror 18. Further, a top light source 24 is provided that is arranged at the wall, adjacent to the mirror 18. In addition, a bottom light source 26 is provided that is arranged at a bottom end of the mirror 18. In addition, side light sources, etc. may be present.

The personal care setting 10 further involves a sensing unit 30 involving a first sensor 32 and a second sensor 34. Generally, the sensing unit 30 includes at least one image sensor 32, 34. The sensors 32, 34 in the exemplary arrangement of FIG. 1 are spaced away from one another and arranged in the vicinity of the mirror 18. In some exemplary embodiments, a so-called smart mirror is provided that implements at least one of a light source and an image sensor. In a smart mirror, the light source and/or the image sensor are not or only barely visible from the front of the mirror.

The at least one image sensor 32, 34 of the sensing unit 30 may involve a camera including a pattern of CCD-elements, CMOS-elements, etc. Preferably, the at least one sensor 32, 34 is capable of detecting electromagnetic radiation both in the visible range and in the invisible range.

Figure 2:
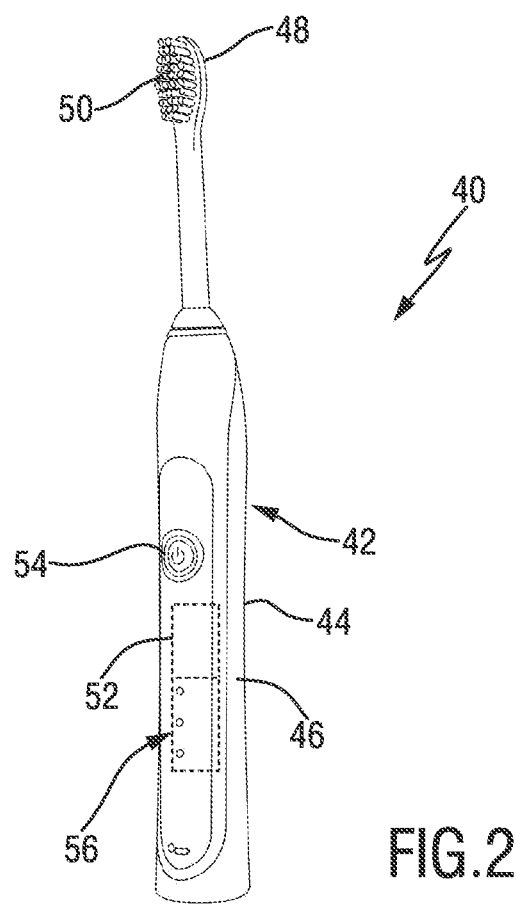
FIG. 2 is a perspective view of an exemplary embodiment of a personal care appliance that is arranged as a toothbrush.

In FIG. 2, a personal care appliance 40 is shown. In exemplary embodiments, the personal care appliance 40 is arranged as a motor-powered toothbrush 42. The personal care appliance 40 includes a housing 44 in which, for instance, a motor, a drive train, a battery, controls, etc. may be arranged. Further, at a top end of the housing 44, a processing head 48 is provided. In the exemplary embodiment of the personal care appliance 40 shown in FIG. 2, the processing head 48 is arranged as a brush head 50.

Further, the personal care appliance 40 comprises an operation control unit 52 that controls the operation thereof. In addition, controls 54 are provided, for instance an on/off button, etc. As already indicated further above, the hand-held personal care appliance 40 incorporates a close-up (contact) sensing unit 56 that is arranged at a handle 46 of the housing 44. Hence, when the user grabs the appliance 40 and performs a personal care procedure, the hand of the user, particularly the palm, contacts sensing elements of the sensing unit 56.

Figure 3:
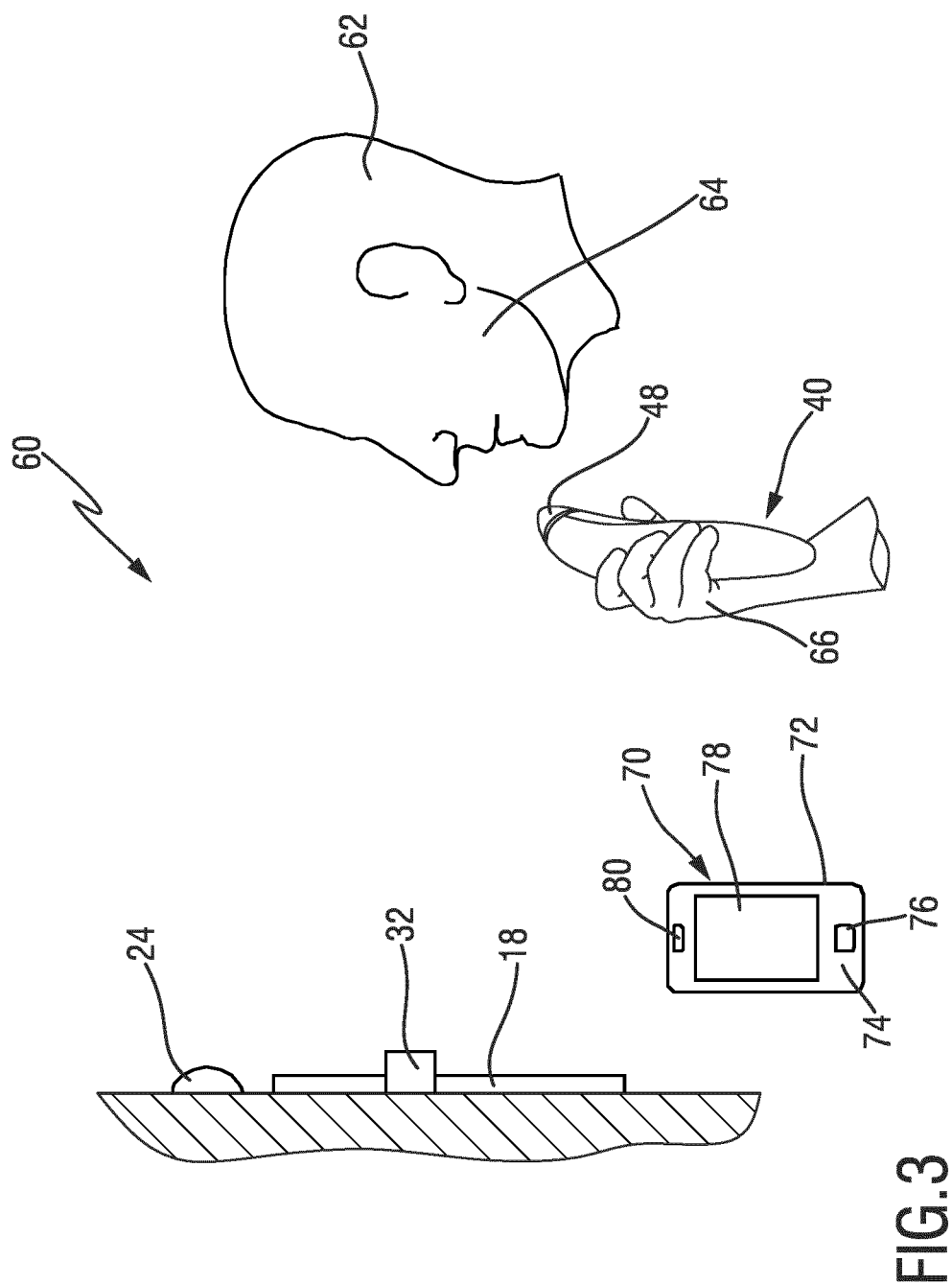
FIG. 3 is a simplified schematic view of an exemplary embodiment of a system for monitoring a state of well-being that is implemented in a personal care environment.

FIG. 3 is a schematic simplified lateral view of a system 60 for monitoring a state of well-being on an individual (referred to hereinafter as user). In FIG. 3, the user 62 is positioned in front of a mirror 18. A head portion (indicated by 64) and a hand portion (indicated by 66) are indicated in FIG. 3. As discussed further above, the user 62 is holding a personal care appliance 40 in his hand 66. Hence, the palm and/or the fingers of the hand 66 contact a housing of the appliance 40. The appliance 40 comprises a processing head 48 to perform a personal care treatment.

As with the embodiment illustrated in FIG. 1, adjacent to the mirror 18, a light source 24 and an image sensor 32 are provided. Preferably, the light source 24 and the image sensor 32 are capable of PPG (photoplethysmography) monitoring. Hence, skin color, perfusion and similar information may be remotely detected when observing the skin portion (face portion) 64 of the user 62.

Quite recently, photoplethysmographic (PPG) systems that operate on a remote basis have been introduced. Generally, PPG systems are used in the field of vital signs detection. Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heartbeat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Quite recently, also non-contact, remote PPG (R-PPG) devices for unobtrusive measurements that are operable in home user environments have been introduced. Remote PPG is a non-invasive technique which measures the small changes in color under the skin epidermis, caused by variations in volume and oxygen saturation of the blood in the vessels, due to heart beats.

Remote PPG utilizes light sources or, more generally, radiation sources disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Using remote PPG technology, vital signs can be measured from video camera signals providing a time sequence of image frames, as it is revealed by minute light absorption changes in the skin caused by the pulsating blood volume.

Verkruysse et al., "Remote plethysmographic imaging using ambient light", Optics Express, 16 (26), 22 Dec. 2008, pp. 21434-21445 demonstrates that photoplethysmographic signals can be measured remotely using ambient light and a conventional consumer level video camera.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation.

An example for an extended application of PPG techniques is disclosed in WO 2016/096591 A1 that relates to a method and a corresponding device for use in allergy testing, the method comprising:

receiving a first set of spatially distributed light intensity values covering a skin region of the subject including a location at which the substance has been applied, wherein the light intensity values in the first set are intensities of visible light, receiving a second set of spatially distributed light intensity values covering the skin region, wherein the light intensity values in the second set are intensities of infrared, IR, light, generating a first spatial distribution of PPG pulse amplitudes based on the first set of light intensity values, generating a second spatial distribution of PPG pulse amplitudes based on the second set of light intensity values, comparing the first spatial distribution to the second spatial distribution, and to the location at which the substance has been applied, and outputting an indication of whether the subject is experiencing an allergic reaction to the substance based on the comparing.

Further fields of application are conceivable. It has been realized that remote, non-obtrusive PPG techniques are also suitably applicable in the non-medical field, e.g. in the personal care field. A main benefit of a camera-based remote PPG monitoring approach is that a considerably large area may be observed.

Reference is made again to FIG. 3. Information obtained by the image sensor 32 may be regarded as stress level indicative information. The stress level indicative information is transferred to a control unit 70. In the exemplary embodiment shown in FIG. 3, the control unit 70 is integrated in a hand-held computing device 72. The device 72 may be arranged, for instance, as a mobile phone, a mobile computer, a tablet computer, etc. Needless to say, the control unit 70, in the alternative, may also be integrated in or directly coupled to one of the personal care appliance 40, the illumination unit 20 and/or the sensing unit 30 (refer to FIG. 1).

In the control unit 70, a processor or processing unit 74 is provided. Further, user controls 76 are present. In addition, a display 78 is provided which may be arranged as a touch-sensitive display. Further, a speaker 80 may be provided.

The control unit 70 provides sufficient computing capacity to process the data provided by the at least one sensor 32. The data provided by the sensor 32 may be referred to as first sensor data or, in certain embodiments, as image data. In this way, stress level indicative information may be obtained from the skin portion 64, preferably using PPG techniques. Further, since the image sensor 32 is arranged to monitor a considerably large region, also the position of the personal care appliance 40 (with respect to the skin portion 64 of the user 62) may be detected and tracked. In this way, the position of the personal care appliance 40 and a "map" of the skin portion 64 of the user 62 may be correlated. In other words, one and the same information (data stream of images) may be used and processed for two analyzes, i.e. position detection/tracking and stress detection. This is not possible with conventional contact PPG devices.

As a consequence, whenever a certain likelihood of an increased stress level is detected, appropriate counter measures may be applied. To this end, the control unit 70 may be arranged to notify the user of the personal care appliance accordingly.

Further, also information obtained by any sensor that is arranged at the personal care appliance 40 and therefore in contact with the hand 66 may be transferred to the control unit 70 at the hand-held computing device 72.

Figure 6:
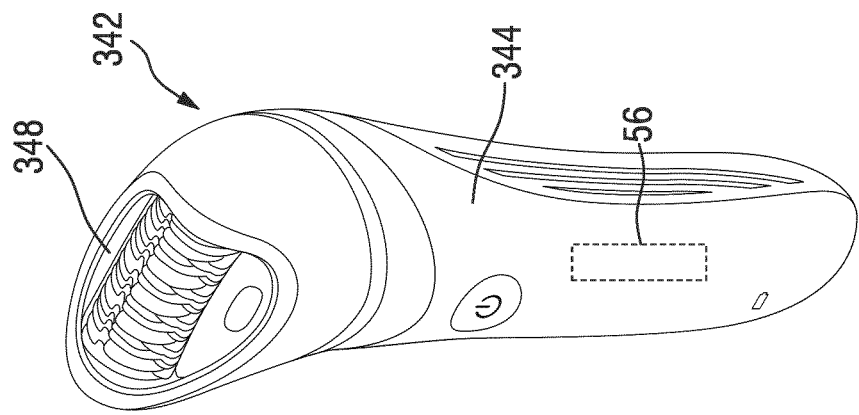
FIG. 6 is a perspective view of an exemplary embodiment of a personal care appliance that is arranged as a hair removal appliance.
Figure 5:
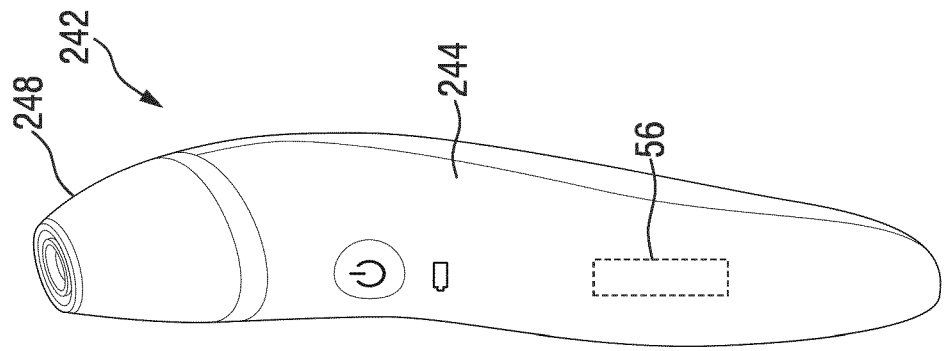
FIG. 5 is a perspective view of an exemplary embodiment of a personal care appliance that is arranged as a skin treatment appliance.
Figure 4:
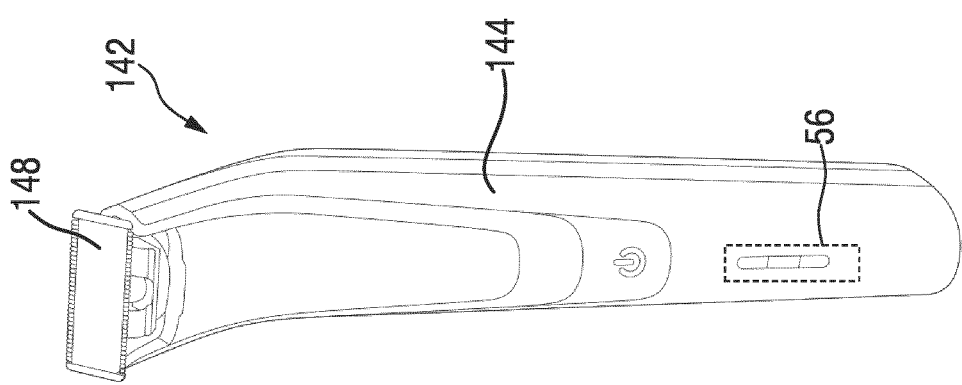
FIG. 4 is a perspective view of an exemplary embodiment of a personal care appliance that is arranged as a hair cutting appliance.

Reference is made to FIG. 4, FIG. 5 and to FIG. 6, each illustrating another exemplary embodiment of a personal care appliance within the context of the present disclosure.

FIG. 4 shows a personal care appliance that is arranged as a hair cutting appliance 142. The hair cutting appliance 142 comprises a housing 144 at a top end of which a processing head 148 including a shaving or trimming section is provided. FIG. 5 shows a personal care appliance that is arranged as a skin treatment appliance 242. The appliance 242 comprises a housing 244 and a processing head 248 that is arranged to apply a skin treatment to a skin portion of the user.

FIG. 6 shows a further embodiment of a personal care appliance that is arranged as a hair removal appliance 342. The appliance 342 may also be referred to as epilator. The appliance 342 comprises a housing 344 at a top end of which a processing head 348 is provided that comprises a hair removal section.

In each of the appliances 142, 242, 342 shown in FIG. 4, FIG. 5 and FIG. 6, a close-up or contact sensing unit 56 is provided. As already indicated further above, the sensing unit 56 may comprise a plurality of sensors, for instance PPG-sensors, temperature sensors, galvanic skin response sensors, etc. When the user grabs a handling section of the respective housing 144, 244, 344 of the appliances 142, 242, 342, the sensing units 56 contact the skin of the holding hand of the user.

Figure 7:
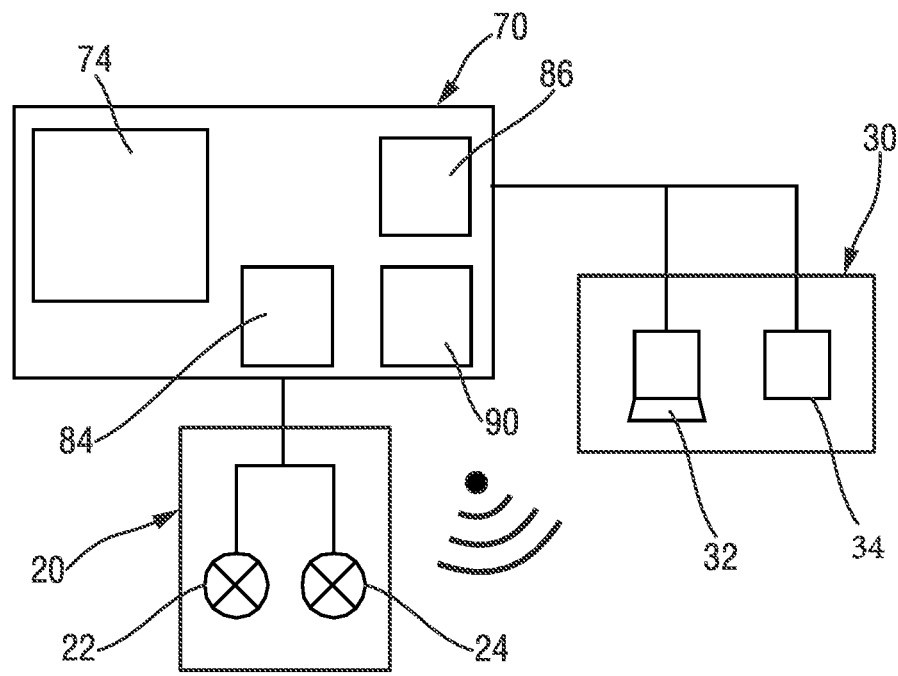
FIG. 7 is a further schematic simplified view of another exemplary embodiment of a system for monitoring a state of well-being.
Figure 7:
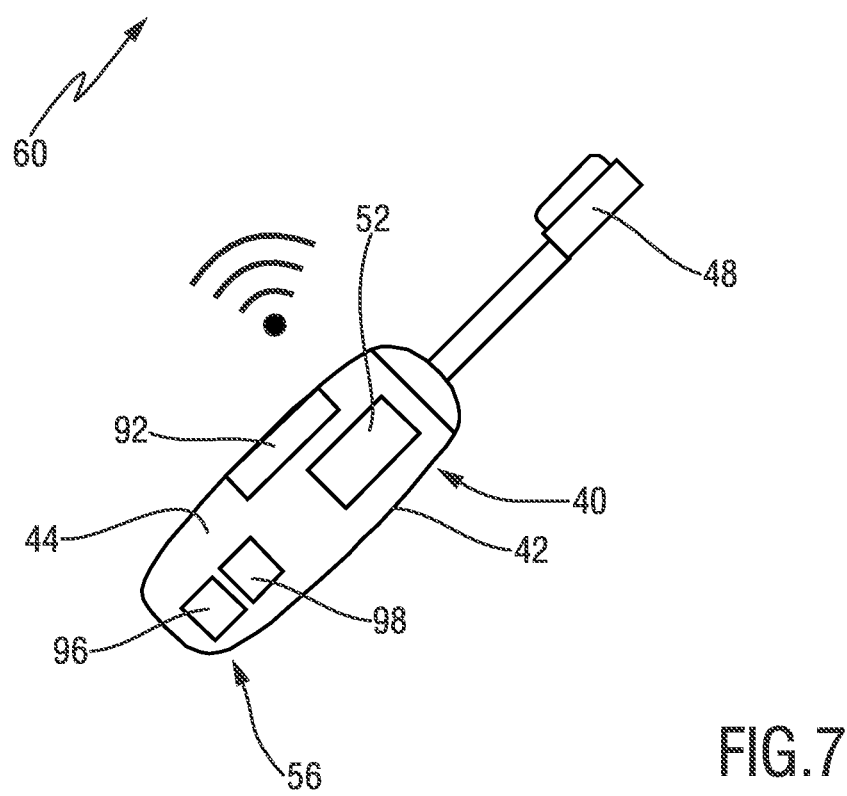

In FIG. 7, a further exemplary setting of a monitoring system 60 that is operable to monitor a state of well-being is illustrated. As with the embodiment shown in FIG. 3, a control unit 70 is provided that is operatively coupled with a sensing unit 30 and an illumination unit 20. The control unit 70, however, is further operatively coupled with a sensing unit 56 at a hand-held personal care appliance 40. The illumination unit 20 comprises a first light source 22 and a second light source 24, for instance. The sensing unit 30 is provided with a first image sensor 32 and a second image sensor 34. In some embodiments, at least one of the image sensors 32, 34 is capable of thermal imaging.

In addition to the processing unit (for instance, central processing unit) 74, the control unit 70 may be provided with an illumination control 84 and a sensor control 86. Hence, the control unit 70 is operatively coupled with the sensing unit 30, the sensing unit 56 and, at least in some embodiments, with the illumination unit 20.

The control unit 70 is further equipped with a communication interface 90. Similarly, the personal care appliance 40 which is also shown in FIG. 7 may be equipped with a communication interface 92. In the exemplary embodiment of FIG. 7, the communication interfaces 90, 92 are arranged for wireless communication. Via the communication interfaces 90, 92, the control 70 may be supplied with sensor data obtained by the sensing units 30, 56.

The personal care appliance 40 shown in FIG. 7 is exemplified as a toothbrush 42. The appliance 40 comprises a housing 44 at an end of which a processing head 48 is provided. Further, an operation control unit 52 to control the (primary) personal care treatment function of the appliance 40 is provided. In addition, at a portion of the housing 44 that is contacted by the user's hand when the appliance 40 is operated, the close-up sensing unit 56 is present. In the embodiment shown in FIG. 7, the sensing unit 56 comprises a first sensor 96 and a second sensor 98 that may be referred to as close-up sensors. The sensors 96, 98 may be arranged to provide second sensor data or, more particularly, supplemental sensor data.

One of the sensors 96, 98 may be arranged as a contact PPG-sensor. One of the sensors 96, 98 may be arranged as a temperature sensor. One of the sensors 96, 98 may be arranged as a galvanic skin response sensor, for instance. Hence, in accordance with this embodiments, the sensors 96, 98 do not provided image data or image-based data.

Figure 8:
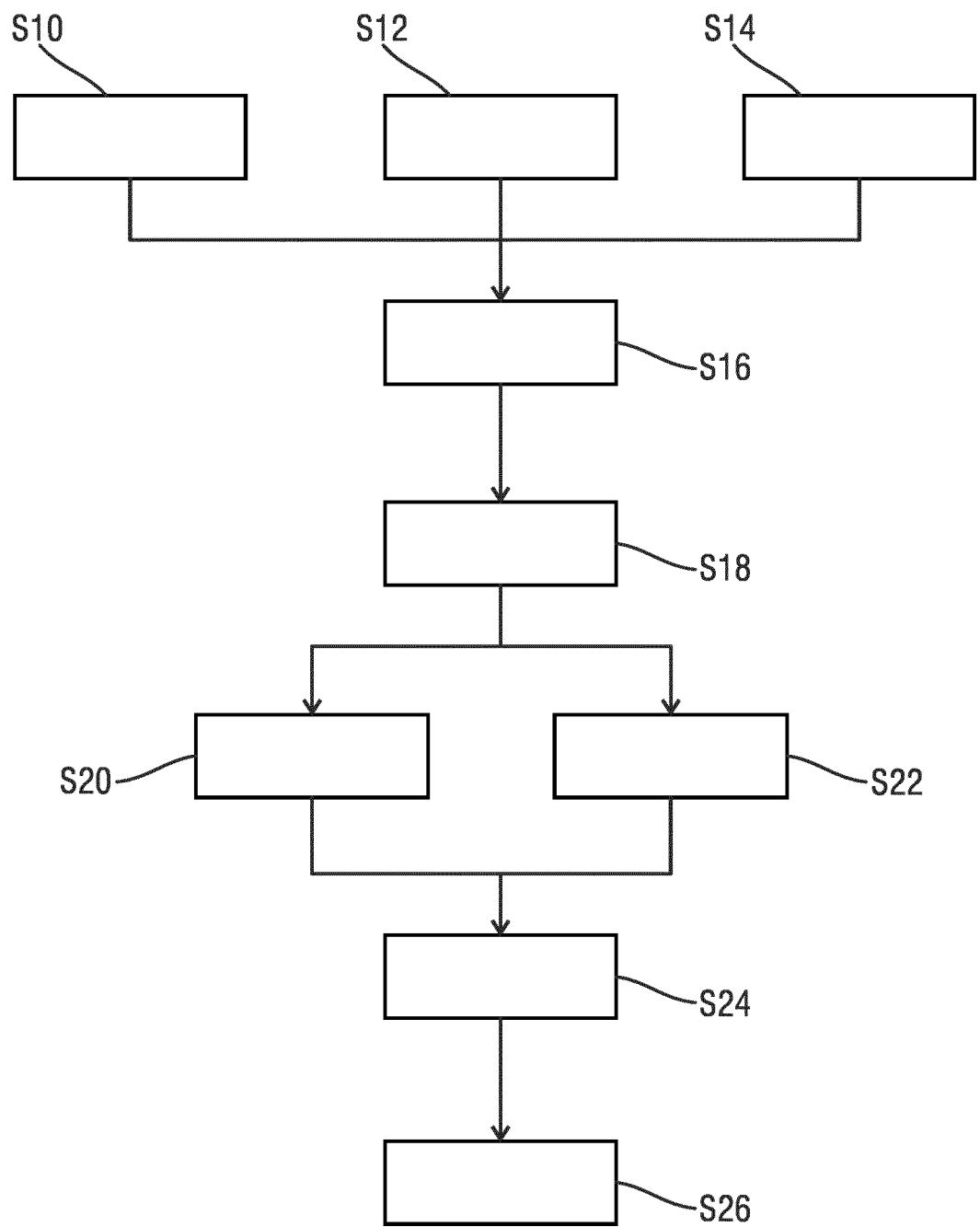
FIG. 8 is a simplified schematic block diagram illustrating an embodiment of a method of monitoring a state of well-being, particularly a stress level, of an individual.

Further reference is made to FIG. 8, showing a block diagram schematically illustrating an exemplary embodiment of a method of monitoring a state of well-being of an individual.

The method involves a step S10 relating to a provision of a personal care appliance that is, however, equipped with so-called close-up sensor equipment. In this way, in addition to a primary personal care feature provided by the appliance, a measurement/detection of physiological signals is enabled. Further, a provision step S12 is provided that relates to the provision of a remotely operating sensing unit. The remotely operating sensing unit may be arranged as a remote PPG sensing unit implementing at least one camera based sensor. Preferably, at least in some embodiments, the remotely operating sensing unit is arranged at or in the vicinity of a mirror and therefore fixedly attached and not arranged to be worn by the user. A further provision step S14 relates to the provision of a control unit that is operable to process signals provided by the close-up sensing unit at the remotely operating sensing unit.

In a further step S16, a respective setting is initialized. This may involve an initial measurement of signals that are potentially indicative of a state of well-being, particularly of a stress level. The step S16 may further involve obtaining reference data for the user's stress level and/or a historical stress level data record.

In a further, subsequent step S18, the personal care appliance is operated. This may involve, for instance, a tooth brushing procedure, a shaving procedure, a skin treatment procedure, a hair removal procedure, etc. Generally, the personal care appliance is a hand-held and manually guided appliance.

Hence, the user typically grabs and holds the appliance in his hand. Therefore, the contact sensors that are provided at the appliance can obtain several data and information regarding the stress level of the user. The respective measurement is performed, so to say, alongside the primary personal care procedure without requiring a lot of or any additional time. Further, also the remotely operating sensing unit may gather respective information as typically the personal care procedure is performed in front of a mirror. Also in this respect, no additional inconvenience is caused. Further, preferably, no additional user intervention is necessary.

The method further involves data processing steps S20 and S22. In the step S20, the data provided by the contact sensing unit is processed. In the basically parallel step S22, the data provided by the remotely operating sensing unit is processed.

Hence, in a further step S24, the data is brought together which enables analysis, particularly relating to characteristic differences in the two rather distinct and remote observed regions. Generally, a set of stress level indicative parameters may be processed.

Eventually, in a step S26, information may be provided that is indicative of a state of well-being or, preferably, of a current stress level of the user. Further, since the personal care procedure may be performed on a daily, weekly or monthly basis, a temporal record may be created in this way. Hence, characteristic, potentially problematic deviations may be detected at an early stage.

Figure 9:
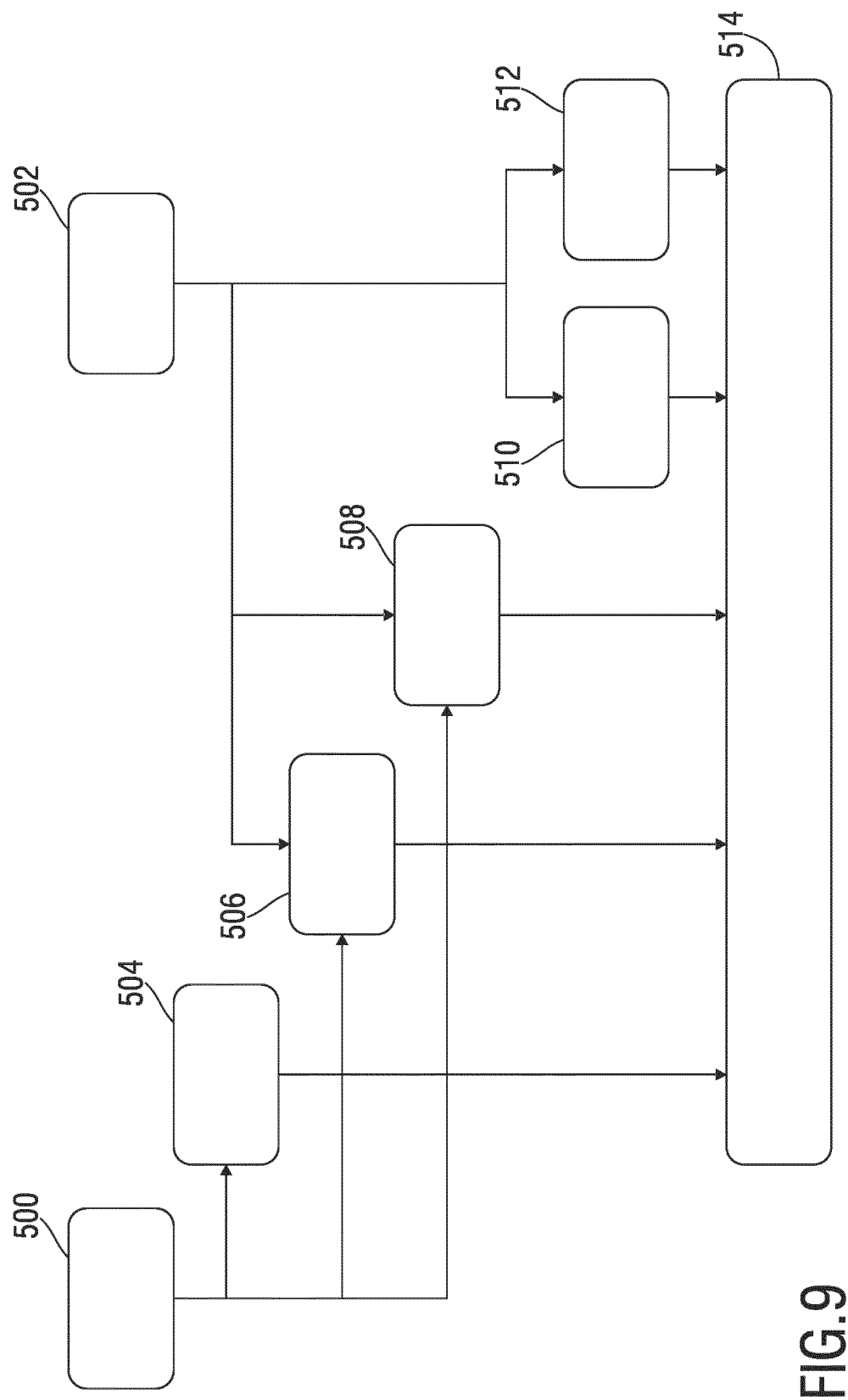
FIG. 9 is a simplified schematic block diagram illustrating an operating principle of a system and a method for monitoring a state of well-being that implement two sensing units one of which is a remotely operating sensing unit and the other one is a close-up (contact) sensing unit.

Additional reference is made to FIG. 9, showing a block diagram that schematically illustrates an exemplary detailed setup and algorithm of a monitoring system/method that can be utilized in the context of stress level detection and monitoring.

Reference numeral 500 indicates a contact, close-up sensing unit that implements a PPG sensor and at least one supplemental sensor, for instance a temperature sensor. A further block indicated by reference numeral 502 relates to a remotely operable sensing unit that is capable of camera based PPG monitoring. Further, the remotely operating sensing unit may be capable of thermal imaging, thereby being equipped for temperature measurements.

Signals provided by the sensing unit 500 may be processed in a block 504 that relates to the calculation of a pulse transit time (PTT) based on two PPG signals. In this way, a blood pressure (BP) representing value may be calculated. Hence, based on PPG signals provided by the block 500, the block 504 may provide a blood pressure parameter.

A downstream block 506 relates to a comparison of PPG signals provided by the block 500 and provided by the block 502. Hence, spatial differences may be detected as PPG signals obtained from the face, for instance, can be compared to PPG signals that are obtained from a palm of a hand, for instance.

A further block 508 relates to a comparison of temperature information provided from each of the blocks 500, 502. Again, spatial discrepancies may be detected.

A further block 510 relates to the analysis of pulse information and breathing information, for instance of a detected pulse rate and breathing rate. The respective values may be compared with the ones obtained in earlier measurements. In this way, a temporal record may be obtained which enables long-term monitoring. Input signals are provided by the remote sensing block 500.

A further block 512 relates to a two-dimensional PPG signal analysis. Input signals are provided by the remote sensing block 500. Camera based PPG measurement equipment may provide images covering a certain region. Hence, within this region, discrepancies may be present which can be detected in the block 512. Further, the block 512 may relate to historical analysis. Again, current data may be compared to data obtained earlier.

The information provided by the blocks 500 and 502 that is processed, computed and analyzed in the blocks 504, 506, 508, 510, 512 may be transmitted to an assessment block 514. The block 514 may also be referred to as stress level assessment block. A set of parameters is transmitted to the block 514. A nominal-actual comparison may be applied to the obtained parameters. Further, thresholding may be applied. For instance, when it is detected that a certain number of the obtained parameters is beyond or below a defined threshold, it may be assessed that a potentially problematic stress level is present.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for monitoring a state of well-being of an individual, the system comprising:
    two distinct sensing units comprising:
        a remotely operating camera-based photoplethysmography (PPG) sensing unit comprising at least one image sensor arranged to remotely monitor a skin portion of a head region of a user, and
        a close-up sensing unit provided at a hand-held personal care appliance, the close-up sensing unit being arranged to monitor a physiological signal of the user through a contact with a hand of the user,
    wherein the monitoring of the physiological signal is temporally aligned with the remote monitoring of the skin portion of the user, and
    a control unit arranged to process first sensor data provided by the remotely operating camera-based PPG sensing unit and second sensor data provided by the close-up sensing unit,
    wherein: the control unit is arranged to process, based on the processed first sensor data and second sensor data, at least one well-being parameter; the at least one well-being parameter is determined based on both image data and supplemental sensor data, the supplemental sensor data's being acquired by spot measurements from the close-up sensing unit that do not involve image detection; and the control unit is arranged to provide, based on the at least one processed well-being parameter, well-being information that is indicative of a current stress level of the user, and
    wherein the system is operable while performing a personal care procedure with the hand-held personal care appliance.

2. The system as claimed in claim 1, wherein the remotely operating camera-based PPG sensing unit that is arranged to obtain signals based on which of a pulse rate and respiration rate of the user is detected, wherein the close-up sensing unit is a contact PPG sensing unit, wherein the remotely operating camera-based PPG sensing unit and the close-up sensing unit are arranged to monitor two distinct and remote body regions of the user, wherein the control unit is arranged to determine a pulse transit time based on PPG information obtained from the two distinct body and remote regions, and to determine a blood pressure based on the pulse transit time.

3. The system as claimed in claim 1, wherein the remotely operating camera-based PPG sensing unit is arranged to detect image data and the control unit is arranged to process the image data in a visible range and in a non-visible range.

4. The system as claimed in claim 1, wherein the remotely operating camera-based PPG sensing unit is arranged to monitor a face portion of the user.

5. The system as claimed in claim 1, wherein the close-up sensing unit is arranged as a contact PPG sensing unit.

6. The system as claimed in claim 5, wherein the control unit is arranged to process PPG information obtained from different body regions of the user.

7. The system as claimed in claim 5, wherein the remotely operating camera-based sensing unit is arranged to detect a first PPG signal based on which a pulse rate and a respiration rate is obtained, and wherein the close-up sensing unit is arranged to detect a second PPG signal based on which a blood pressure parameter is obtained.

8. The system as claimed in claim 7, wherein the control unit is arranged to detect and analyze differences between characteristics of the first PPG signal and the second PPG signal.

9. The system as claimed in claim 7, wherein the first PPG signal involves a 2D PPG distribution, and wherein the control unit is arranged to detect spatial discrepancies in the first PPG signal.

10. The system as claimed in claim 1, wherein the control unit is arranged to process a set of stress level indicative parameters, to perform a threshold analysis for the set of stress level indicative parameters, and to determine, based thereon, a current stress level of the user.

11. The system as claimed in claim 1, wherein the at least one image sensor of the remotely operating camera-based sensing unit is arranged at or in a vicinity of a mirror.

12. The system as claimed in claim 11, wherein the remotely operating camera-based sensing unit is provided with or operatively coupled to at least one illumination source that is operable to illuminate the monitored head portion of the user.

13. The system as claimed in claim 1, wherein the hand-held personal care appliance is one of a grooming appliance, a dental care appliance, a massage appliance, and a skin care appliance.

14. A method of monitoring a state of well-being of an individual, the method comprising:
providing two distinct sensing units comprising:
providing a remotely operating camera-based photoplethysmography (PPG) sensing unit that comprises at least one image sensor arranged to remotely monitor a skin portion of a head region of a user,
providing a hand-held personal care appliance that is equipped with a close-up sensing unit that is arranged to monitor a physiological signal of the user through a contact with a hand of the user,
wherein the monitoring of the physiological signal is temporally aligned with the remote monitoring of the skin portion of the user,
providing a control unit that is arranged to process first sensor data provided by the remotely operating camera-based PPG sensing unit and second sensor data provided by the close-up sensing unit,
performing a personal care procedure with the hand-held personal care appliance,
processing, based on the processed first sensor data and second sensor data, at least one well-being parameter while performing the personal care procedure with the hand-held personal care appliance, wherein the well-being parameter is determined based on both image data and supplemental sensor data, the supplemental sensor data's being acquired by spot measurements from the hand-held personal care appliance that do not involve image detection, and
determining, based on the at least one processed parameter, well-being information that is indicative of a current stress level of the user.

15. A non-transitory computer-readable medium, which stores instructions, which when executed by a processor, cause the processor to:
process first sensor data provided by a remotely operating camera-based photoplethysmography (PPG) sensing unit and second sensor data provided by a close-up sensing unit performing a personal care procedure with a personal care appliance;
process, based on the processed first sensor data and second sensor data, at least one well-being parameter while performing a personal care procedure with the personal care appliance; and
determine, based on at least one processed well-being parameter, well-being information that is indicative of a current stress level of a user, wherein the at least one well-being parameter is determined based on both image data and supplemental sensor data, the supplemental sensor data's being acquired by spot measurements from the close-up sensing unit that do not involve image detection.

16. The non-transitory computer-readable medium of claim 15, wherein the instructions, when executed by the processor, further cause the processor to:
process image data in a visible range and in a non-visible range.

17. The non-transitory computer-readable medium of claim 15, wherein the instructions, when executed by the processor, further cause the processor to:
process PPG information obtained from different body regions of a user.

18. The non-transitory computer-readable medium of claim 17, wherein the instructions, when executed by the processor, further cause the processor to:
determine a pulse transit time based on the processed PPG information obtained from two body regions; and
determine a blood pressure based on the pulse transit time.

19. The non-transitory computer-readable medium of claim 15, wherein the instructions, when executed by the processor, further cause the processor to:
detect and analyze differences between characteristics of a first PPG signal and a second PPG signal.

20. The non-transitory computer-readable medium of claim 19, wherein the first PPG signal involves a 2D PPG distribution, and wherein the instructions, when executed by the processor, further cause the processor to detect spatial discrepancies in the first PPG signal.

* * * * *